US009114035B2

(12) United States Patent
Oberti et al.

(10) Patent No.: US 9,114,035 B2
(45) Date of Patent: Aug. 25, 2015

(54) APPARATUS AND METHOD FOR TREATING CARDIOVASCULAR DISEASES

(75) Inventors: Carlos Oberti, Cleveland, OH (US); Jose Luis Navia, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1337 days.

(21) Appl. No.: 11/789,827

(22) Filed: Apr. 26, 2007

(65) Prior Publication Data

US 2007/0255389 A1 Nov. 1, 2007

Related U.S. Application Data

(60) Provisional application No. 60/795,256, filed on Apr. 26, 2006.

(51) Int. Cl.
| | |
|---|---|
| A61F 2/06 | (2013.01) |
| A61F 2/24 | (2006.01) |
| A61F 2/90 | (2013.01) |
| A61F 2/95 | (2013.01) |
| A61F 2/82 | (2013.01) |
| A61N 1/362 | (2006.01) |

(52) U.S. Cl.
CPC ... *A61F 2/90* (2013.01); *A61F 2/95* (2013.01); *A61F 2002/821* (2013.01); *A61F 2210/0004* (2013.01); *A61F 2210/0076* (2013.01); *A61F 2220/0008* (2013.01); *A61F 2220/0016* (2013.01); *A61F 2230/0054* (2013.01); *A61F 2230/0078* (2013.01); *A61F 2250/003* (2013.01); *A61F 2250/0067* (2013.01); *A61N 1/362* (2013.01)

(58) Field of Classification Search
USPC .................................................. 623/1.44
See application file for complete search history.

(56) References Cited

U.S. PATENT DOCUMENTS

| | | | |
|---|---|---|---|
| 5,178,618 A | 1/1993 | Kandarpa | |
| 6,416,548 B2 | 7/2002 | Chinn et al. | |
| 6,579,308 B1 * | 6/2003 | Jansen et al. | 623/1.15 |
| 6,632,223 B1 * | 10/2003 | Keane | 606/41 |
| 6,685,739 B2 * | 2/2004 | DiMatteo et al. | 623/1.24 |
| 6,716,242 B1 | 4/2004 | Altman | |
| 6,805,706 B2 * | 10/2004 | Solovay et al. | 623/1.15 |
| 6,926,714 B1 | 8/2005 | Sra | |
| 7,192,438 B2 * | 3/2007 | Margolis | 607/96 |
| 7,195,628 B2 * | 3/2007 | Falkenberg | 606/41 |
| 7,209,783 B2 * | 4/2007 | Fellows et al. | 607/5 |
| 7,344,559 B2 * | 3/2008 | Gray et al. | 623/1.15 |

(Continued)

*Primary Examiner* — Thomas J Sweet
*Assistant Examiner* — Seema Mathew
(74) *Attorney, Agent, or Firm* — Tarolli, Sundheim, Covell & Tummino LLP

(57) ABSTRACT

An apparatus for treating cardiovascular diseases includes an expandable support member having oppositely disposed proximal and distal end portions and a main body portion between the end portions for positioning in a blood vessel. The proximal end portion of the expandable support member includes a plurality of wing members that extend from the main body portion. Each of the wing members is for engaging at least a portion of an antrum of a cardiac chamber surrounding the blood vessel. At least a portion of the expandable support member is treated with at least one therapeutic agent for eluting into the blood vessel, the cardiac chamber, and/or cardiac tissue. The expandable support member is made of wire-mesh, and at least a portion of the expandable support member may be made of a bioabsorbable material.

21 Claims, 10 Drawing Sheets

(56) References Cited

U.S. PATENT DOCUMENTS

| | | |
|---|---|---|
| 7,367,970 B2 * | 5/2008 | Govari et al. .................. 606/32 |
| 8,097,015 B2 * | 1/2012 | Devellian ...................... 606/200 |
| 8,197,475 B2 * | 6/2012 | Bruszewski et al. ............ 606/41 |
| 8,257,376 B2 * | 9/2012 | Solem ........................... 606/167 |
| 2002/0082682 A1 | 6/2002 | Barclay et al. |
| 2003/0055491 A1 | 3/2003 | Schwartz et al. |
| 2003/0069606 A1 * | 4/2003 | Girouard et al. .................. 607/3 |
| 2003/0139800 A1 * | 7/2003 | Campbell ..................... 623/1.15 |
| 2004/0098106 A1 | 5/2004 | Williams et al. |
| 2004/0116965 A1 * | 6/2004 | Falkenberg ....................... 607/5 |
| 2004/0122506 A1 | 6/2004 | Shanley et al. |
| 2004/0153139 A1 | 8/2004 | Altman |
| 2004/0167598 A1 * | 8/2004 | Margolis ...................... 623/1.11 |
| 2004/0215186 A1 | 10/2004 | Cornelius et al. |
| 2004/0215310 A1 * | 10/2004 | Amirana ...................... 623/1.11 |
| 2004/0220655 A1 * | 11/2004 | Swanson et al. .............. 623/1.11 |
| 2004/0243230 A1 | 12/2004 | Navia et al. |
| 2004/0249443 A1 | 12/2004 | Shanley et al. |
| 2004/0254597 A1 | 12/2004 | Schwartz et al. |
| 2005/0090820 A1 | 4/2005 | Cornelius et al. |
| 2005/0177118 A1 | 8/2005 | Hoganson et al. |
| 2005/0228496 A1 | 10/2005 | Mensah et al. |
| 2005/0234540 A1 * | 10/2005 | Peavey et al. ................. 623/1.18 |
| 2005/0267567 A1 * | 12/2005 | Shalev .......................... 623/1.31 |
| 2006/0009838 A1 | 1/2006 | Shanley et al. |
| 2006/0047338 A1 * | 3/2006 | Jenson et al. ................. 623/2.11 |
| 2006/0259136 A1 * | 11/2006 | Nguyen et al. ............... 623/2.18 |
| 2007/0239272 A1 * | 10/2007 | Navia et al. .................. 623/2.36 |

\* cited by examiner

APPARATUS AND METHOD FOR TREATING CARDIOVASCULAR DISEASES

RELATED APPLICATION

This application claims priority from U.S. Provisional Patent Application Ser. No. 60/795,256, filed on Apr. 26, 2006, the subject matter of which is incorporated herein by reference.

FIELD OF THE INVENTION

The present invention relates to the treatment of cardiovascular diseases, and more particularly relates to an apparatus and method for treating cardiac conditions such as arrhythmias, heart failure, acute and chronic heart transplant rejection, and pulmonary arterial hypertension.

BACKGROUND OF THE INVENTION

The heart is, in essence, a pump that is responsible for circulating blood throughout the body. In a normally functioning heart such circulation is caused by the generation of electrical impulses that, for example, increase or decrease the heart rate and/or the force of contraction in response to the demands of the circulatory system. If the electrical signal becomes disturbed in some way, the efficient pumping action of the heart may deteriorate, or even stop altogether.

Disturbance in the regular rhythmic beating of the heart is a common disorder seen in heart disease. Irregular rhythms (arrhythmia) can be a minor annoyance, or may indicate a serious problem. For example, arrhythmias may indicate an underlying abnormality of the heart muscle, valves or arteries, and includes the situation where the heart is beating too slowly (bradycardia) and also where the heart is beating too rapidly (tachycardia).

One particular type of cardiac arrhythmia, known as atrial fibrillation (AF), is a common cardiac rhythm disorder which can affect the quality of a patient's life and may be associated with significant morbidity. Atrial fibrillation is characterized by a rapid disorganized rhythm of the upper chambers of the heart (the atria). Instead of a single wavefront of electrical activation during regular rhythm, AF consists of multiple coexistent wavefronts with random re-entry. The condition may happen by itself (lone AF), may be related with hypertension, valvular disease, or may arise following cardiac surgery.

In a significant proportion of patients, part of the cause of AF may be traced to the pulmonary veins. The pulmonary veins contain a sleeve of heart muscle in their proximal extension from the left atrium, and episodes of AF are often triggered by rapidly discharging foci in this region. Such rapidly discharging foci may be located as far as several centimeters up a pulmonary vein.

The etiology of AF is varied and has been hypothesized in some cases to have a genetic component. While medication is effective to control AF in some patients, other primary treatment modalities, such as endocardial ablation or surgical intervention, are often necessary for effective treatment. For example, endovascular approaches may be used to create lesions using an ablation catheter to block intra-atrial conduction. Such primary treatments are not always satisfactory, however, as arrhythmias often reoccur in patients (20-50%) and ablation procedures may sometimes result in unwanted sequelae, such as pulmonary vein stenosis or drug inefficiency or side effects by the complementary pharmacological treatment, and thus additional secondary treatments such as additional ablation procedures may be necessitated.

SUMMARY OF THE INVENTION

In accordance with one aspect of the present invention, an apparatus for treating cardiovascular diseases includes an expandable support member having oppositely disposed proximal and distal end portions and a main body portion between the end portions for positioning in a blood vessel. The proximal end portion of the expandable support member includes a plurality of wing members that extend from the main body portion. Each of the wing members is for engaging a portion of an antrum of a cardiac chamber surrounding the blood vessel.

In accordance with another aspect of the present invention, at least a portion of the expandable support member is treated with at least one therapeutic agent for eluting into the blood vessel, the cardiac chamber, and/or cardiac tissue.

In accordance with another aspect of the present invention, at least a portion of the expandable support member is bioabsorbable.

In accordance with another aspect of the present invention, the expandable support member is made of wire-mesh.

In accordance with another aspect of the present invention, a method for treating cardiovascular diseases is provided. An apparatus having an expandable support member is first provided. At least a portion of the expandable support member is treated with at least one therapeutic agent for eluting into a blood vessel, a cardiac chamber, and/or cardiac tissue. The expandable support member is inserted into a cardiac chamber and then advanced until the expandable support member is positioned within at least a portion of the ostium of a blood vessel. The expandable support member is next expanded so that the expandable support member engages the at least a portion of the ostium of a blood vessel, and then secured in at least a portion of the antrum of a cardiac chamber.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF EMBODIMENTS

Figure 1:
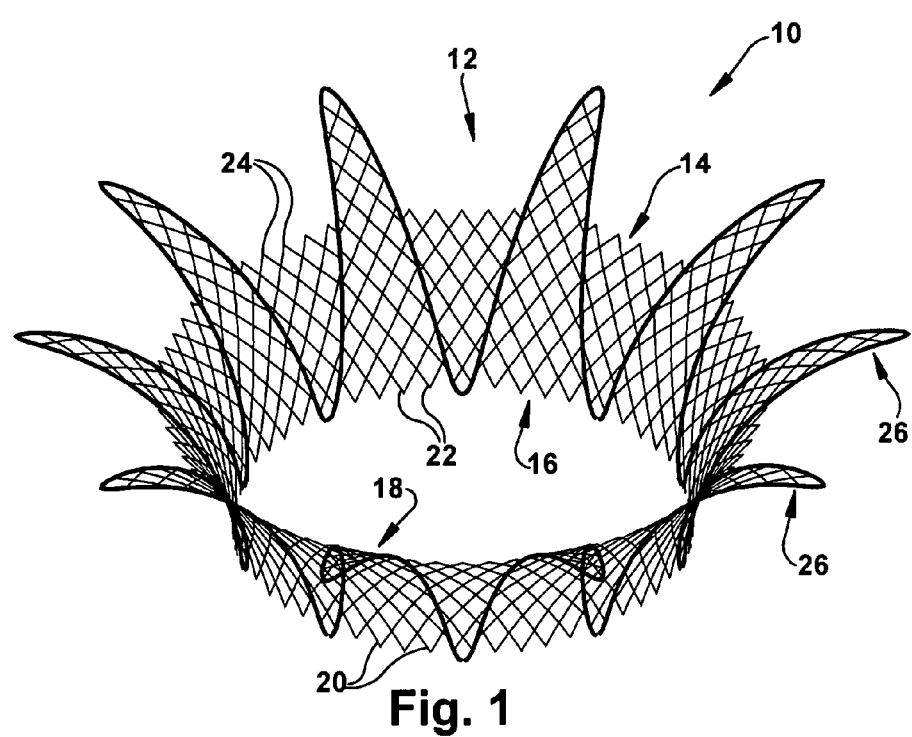
FIG. 1 is a perspective view showing an apparatus, in an expanded configuration, for treating cardiovascular diseases constructed in accordance with the present invention.

The present invention relates to the treatment of cardiovascular diseases, and more particularly relates to an apparatus and method for treating cardiac conditions such as heart failure, arrhythmias, acute and chronic heart transplant rejection, and pulmonary arterial hypertension. As representative of the present invention, FIG. 1 illustrates an apparatus 10 for treating cardiac arrhythmias, such as atrial fibrillation (AF). It should be understood, however, that the apparatus 10 disclosed herein may be used to treat other cardiac arrhythmias including, but not limited to, premature atrial contraction, atrial flutter, supraventricular tachycardia, sick sinus syndrome, atrioventricular block, ventricular fibrillation, premature ventricular contraction, ventricular tachycardia, and other cardiovascular diseases such as heart failure, acute and chronic heart transplant rejection, and pulmonary arterial hypertension. Further, it is contemplated that the apparatus 10 may also be useful as a complimentary treatment to pacemaker implantation and/or defibrillator implantation.

Figure 2:
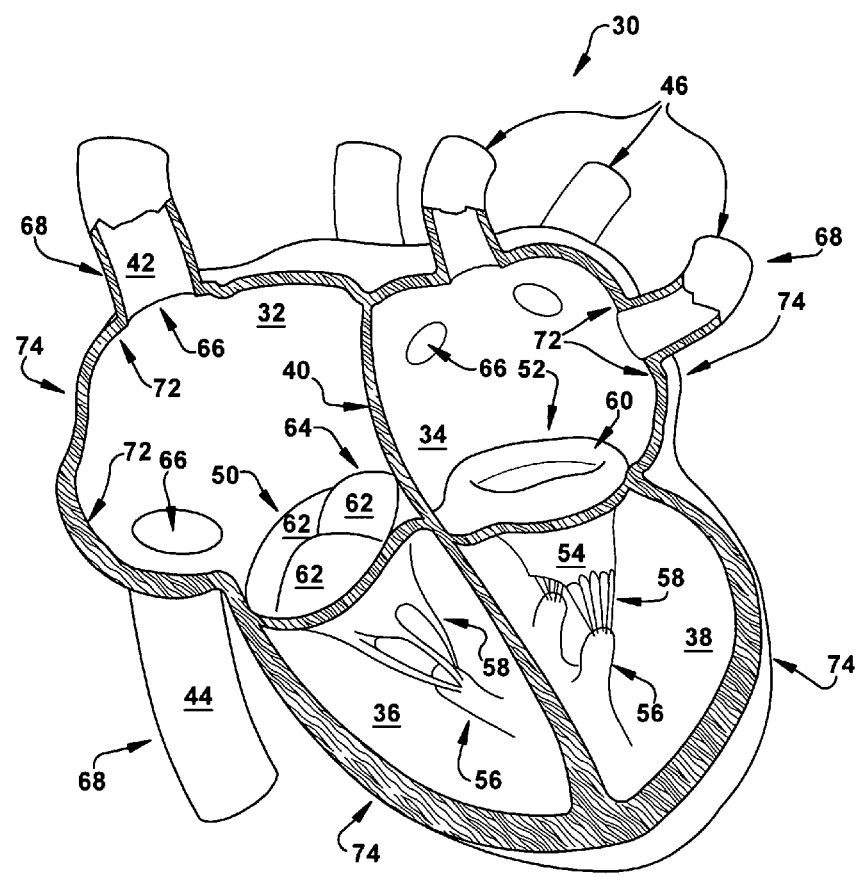
FIG. 2 is a cross-sectional schematic view of a human heart.
Figure 2A:
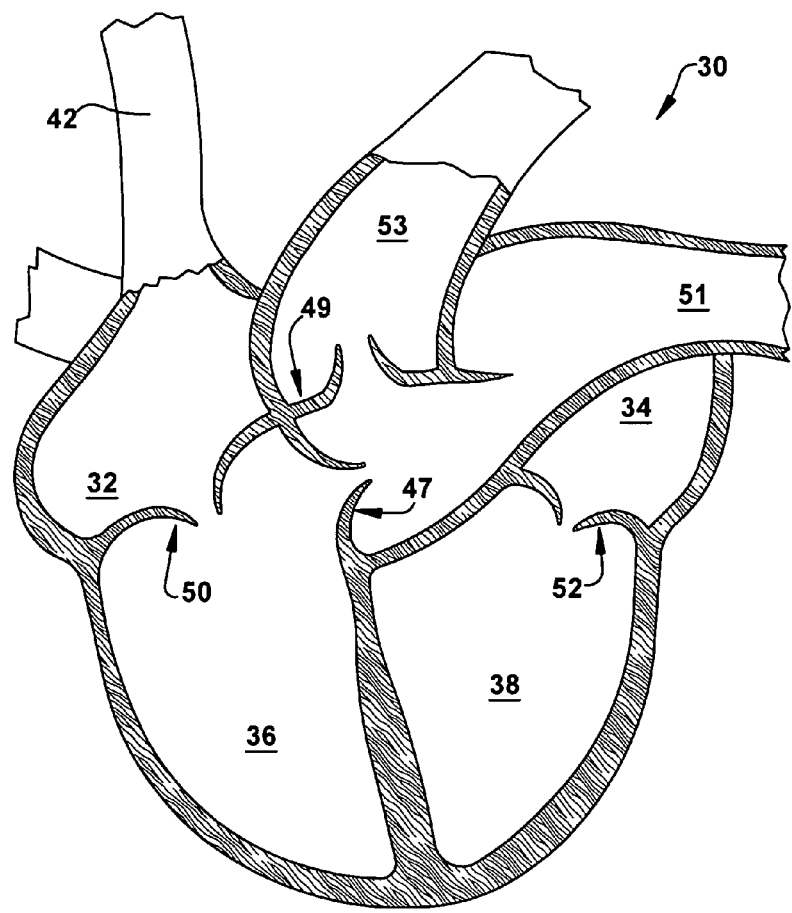
FIG. 2A is different cross-sectional schematic view of the human heart shown in FIG. 2.

FIG. 2 schematically illustrates a human heart 30 which includes four chambers: the right and left atria 32 and 34, and the right and left ventricles 36 and 38, respectively. The right and left atria 32 and 34 are divided by the interatrial septum 40. The thin-walled right atrium 32 receives deoxygenated blood from the superior vena cava 42, the inferior vena cava 44, and from the coronary sinus (not shown). The thin-walled left atrium 34 receives oxygenated blood from pulmonary veins 46. The right and left ventricles 36 and 38 pump deoxygenated and oxygenated blood, respectively, the right ventricle to the pulmonary circuit and the left ventricle throughout the body, and the pocket-like semilunar pulmonary valve 47 (FIG. 2A) and aortic valve 49 prevent reflux into the ventricles. Atrial blood is pumped through the atrioventricular orifices, guarded by the tri-leaflet tricuspid valve 50 (FIGS. 2 and 2A) on the right side of the heart 36 and the bi-leaflet mitral valve 52 on the left side of the heart, while ventricular blood is pumped through the pulmonary artery 51 (FIG. 2A) and the aorta 53 (FIG. 2A). The leaflets 54 (FIG. 2) of the mitral valve 52 are attached to the papillary muscles 56 in the left ventricle 38 by chordae tendineae 58. The leaflets 54 of the mitral valve 52 extend across an annulus 60, which is an area of heart wall tissue at the junction of the atrial and ventricular walls that is relatively fibrous and significantly stronger than leaflet tissue. Similarly, the leaflets 62 of the tricuspid valve 50 are attached to the papillary muscles 56 in the right ventricle 36 by chordae tendineae 58. The leaflets 62 of the tricuspid valve 50 extend across an annulus 64 (not shown in detail) at the junction of the atrial and ventricular walls.

As shown in FIG. 1, the present invention comprises an expandable support member 12 having oppositely disposed proximal and distal end portions 14 and 16 and a main body portion 18 between the end portions. The expandable support member 12 is both flexible and resilient, and, as discussed in more detail below, can be made of a shape memory material such as Nitinol, stainless steel, or other suitable medical grade metals or plastics having shape memory characteristics. Additionally, the expandable support member 12 may be made from a bioabsorbable material including, for example, magnesium alloy, dendrimers, biopolymers such as thermoplastic starch, polyalctides, cellulose, and aliphatic aromatic copolyesters. The expandable support member 12 may also be made of a radio-opaque material or include radio-opaque markers to facilitate fluoroscopic visualization. The flexible and expandable properties of the expandable support member 12 facilitate percutaneous delivery of the expandable support member, while also allowing the expandable support member to conform to a portion of the ostium 66 (FIG. 2) of a blood vessel 68, such as the ostium 70 (FIG. 8) of a pulmonary vein 46.

Figure 3:
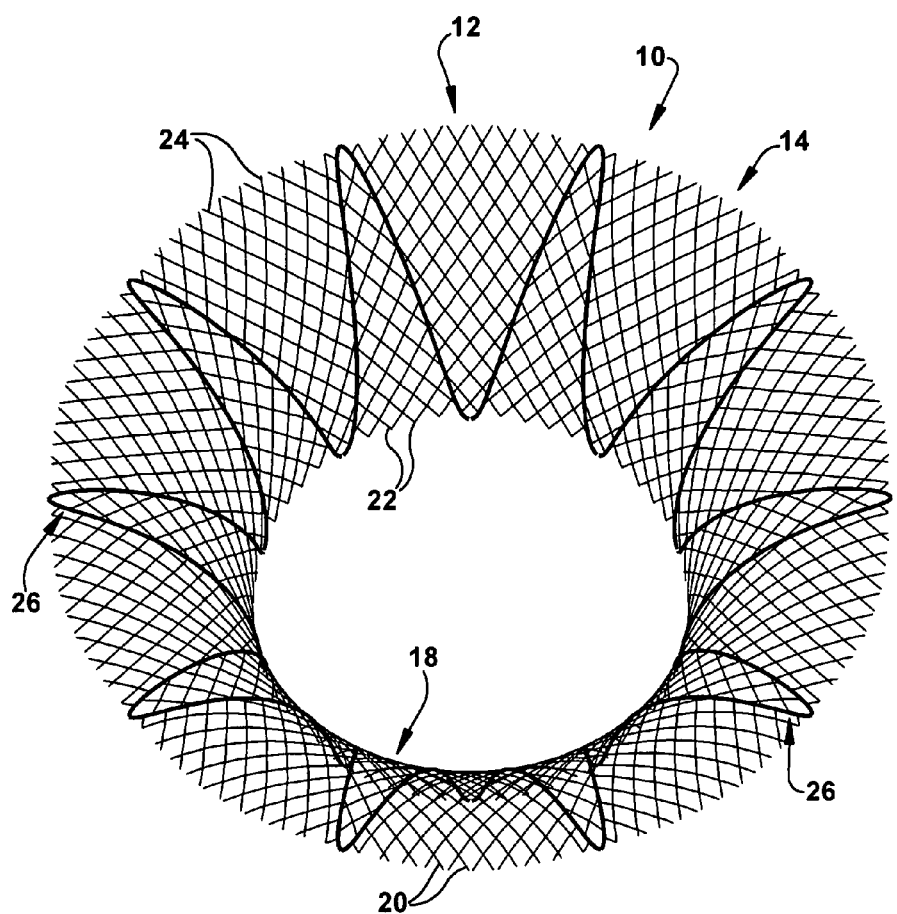
FIG. 3 is a perspective view showing an alternate embodiment of the apparatus in FIG. 1.

The expandable support member 12 (FIG. 1) comprises a continuous series of W-shaped segments 20 collectively forming a mesh-like configuration. It is contemplated, however, that other geometries may be used. The lower tips 22, as viewed in FIG. 1, of the W-shaped segments 20 form the distal end portion 16 of the expandable support member 12, and the upper tips 24 of the W-shaped segments form the proximal end portion 14 of the expandable support member. As shown in FIG. 1, for example, both the wing members 26 and the main body portion 18 of the expandable support member 12 may have a mesh-like configuration. Alternatively, the entire length L (FIG. 4A) of the main body portion 18, including the wing members 26, may have a mesh-like configuration as illustrated in FIG. 3.

Figure 4A:
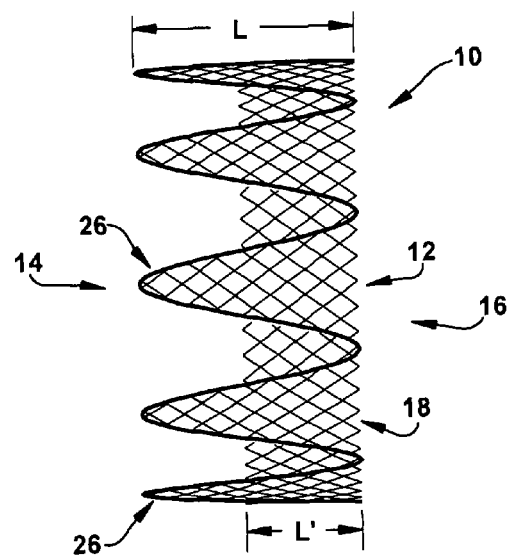
FIG. 4A is a cross-sectional view of the apparatus shown in FIG. 1.
Figure 4B:
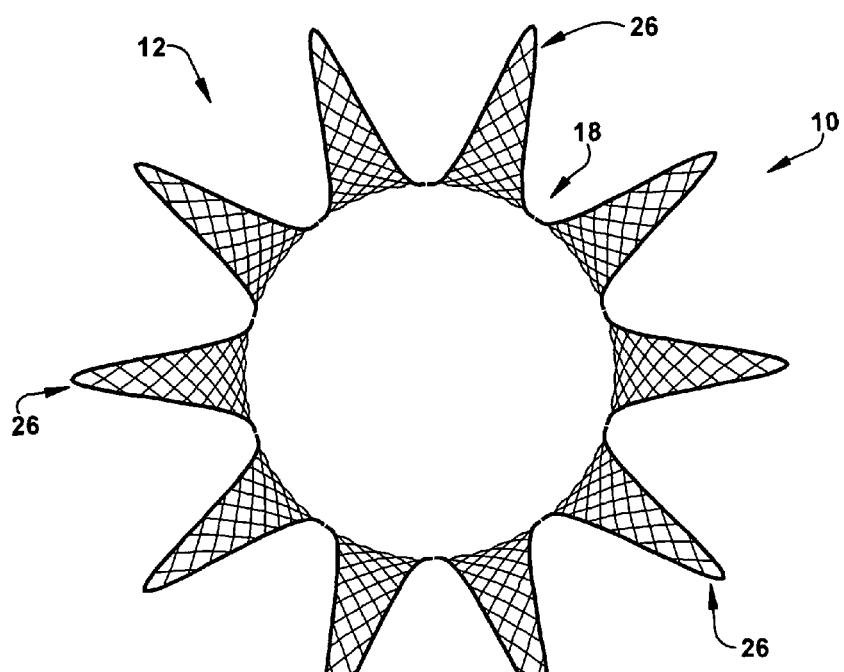
FIG. 4B is a plan view of the apparatus shown in FIG. 1.

Referring to FIGS. 4A and 4B, the main body portion 18 of the expandable support member 12 is defined between the proximal and distal end portions 14 and 16. The main body portion 18 has a generally cylindrical shape and is adapted to conform to the three-dimensional shape of a blood vessel 68 (FIG. 2). The main body portion 18 (FIG. 4A) may also have a conical shape, depending on the geometry of the blood vessel 68 (FIG. 2). The size of the main body portion 18 (FIG. 4B) may be varied as needed. For example, the circumference and/or diameter of the main body portion 18 may be varied so that the expandable support member 12 more readily conforms to the shape of the blood vessel 68 (FIG. 2). Additionally or optionally, the length L' (FIG. 4A) of the main body portion 18 may also be increased or decreased as needed.

Figure 5:
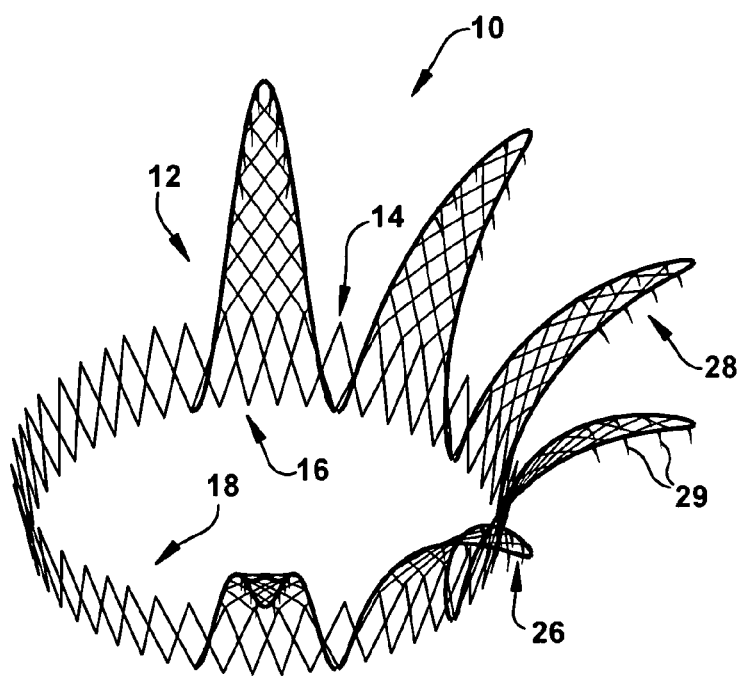
FIG. 5 is a perspective view showing an alternative embodiment of the apparatus in FIG. 1.

The proximal end portion 14 of the expandable support member 12 comprises a plurality of wing members 26 that resemble arches and which extend integrally from the main body portion 18 generally in the proximal direction. In the embodiment illustrated in FIG. 1, there are eleven wing members 26 spaced about the circumference of the proximal end portion 14, but it should be understood that more or less than eleven wing members may be used. As shown in FIG. 5, for example, there may be six wing members 26 spaced about the circumference of the proximal end portion 14. The apparatus 10 shown in FIG. 5 may be useful for matching the vascular anatomy. For example, the apparatus 10 may be implanted into the ostium of a superior vena cava 42, as shown in FIGS. 2 and 2A, where a portion of the right atrium wall is nearly flush with the lumen of the superior vena cava.

Figure 7:
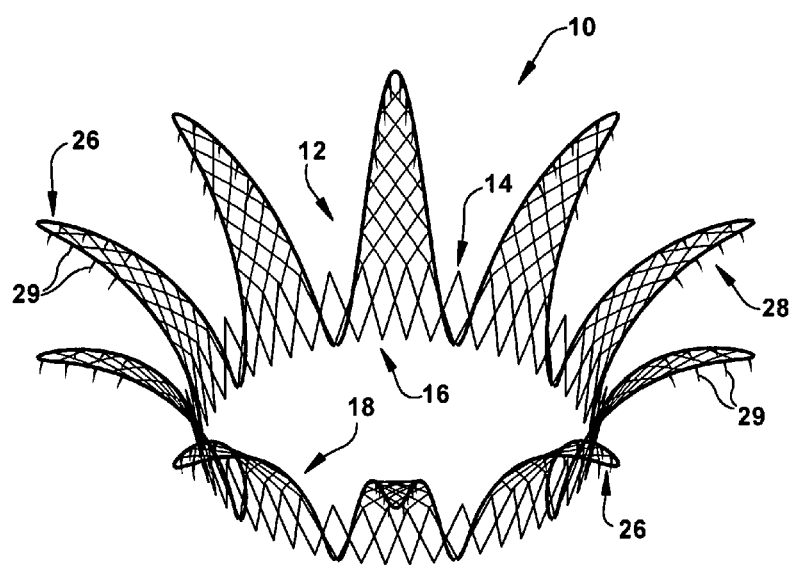
FIG. 7 is a perspective view showing another alternative embodiment of the apparatus in FIG. 1.

The wing members 26 are shaped for conforming to the shape of an antrum 72 (FIG. 2) of a cardiac chamber 74 surrounding a blood vessel 68. The wing members 26 (FIG. 1) are resiliently bendable and are movable from the radially collapsed configuration of FIG. 10 (not shown in detail) to the radially expanded condition of FIG. 1 for delivery and placement of the expandable support member 12. Each wing member 26 may also include at least one attachment mechanism 28 (FIG. 7), such as a hook member 29 or barb, for embedding into a cardiac 73 (FIG. 2) of the antrum 72 of a cardiac chamber 74 to help secure the expandable support member 12 (FIG. 1) in the ostium 66 of a blood vessel 68 (FIG. 2).

At least a portion of the expandable support member 12 (FIG. 1) is treated with at least one therapeutic agent for eluting into a blood vessel 68, a cardiac chamber 74, and/or cardiac wall 73. The therapeutic agent is capable of preventing a variety of pathological conditions including, but not limited to, arrhythmias, thrombosis, stenosis, apoptosis, and inflammation. Accordingly, the therapeutic agent may include at least one of an anti-arrhythmic agent, anticoagulant, an antioxidant, a fibrinolytic, a steroid, an anti-apoptotic agent, an anti-overgrowth agent (i.e., capable of preventing epithelial cell overgrowth), and/or an anti-inflammatory agent. Optionally or additionally, the therapeutic agent may be capable of treating or preventing other disease or disease processes such as microbial infections and heart failure. In these instances, the therapeutic agent may include an anti-microbial agent, an inotropic agent, a chronotropic agent, and/or a biological agent such as a cell or protein. More specific types of these therapeutic agents are listed below, including other types of therapeutic agents not discussed above.

A plurality of portions of the expandable support member 12 (FIG. 1) may be separately treated with a different one of the therapeutic agents. For example, the main body portion 18 may be treated with an anti-inflammatory agent while each of the wing members 26 is separately treated with an anti-coagulant. Alternatively, each of the wing members 26 may be separately treated with a different therapeutic agent. By treating the expandable support member 12 with different therapeutic agents, cardiac arrhythmias, as well as different medical sequelae associated with primary catheter-based treatments for cardiac arrhythmias, can be simultaneously treated. Implanting the apparatus 10 in a pulmonary vein 46 (FIG. 2) following an ablative surgical intervention, for example, may induce partial or complete mechanical, electrical, and/or pharmacological isolation of dysfunctional electrical impulses emanating from the pulmonary vein by the localized delivery of at least one therapeutic agent to the post-ablative site. It should be appreciated that the expandable support member 12 may be treated with any combination and/or variation of the therapeutic agents mentioned above and discussed further below.

Examples of acceptable therapeutic agents include heparin, synthetic heparin analogues (e.g., fondaparinux), G(GP) $II_b/III_a$ inhibitors, vitronectin receptor antagonists, hirudin, antithrombin III, drotrecogin alpha; fibrinolytics such as alteplase, plasmin, lysokinase, factor XIIa, factor VIIa, prourokinase, urokinase, streptokinase; thrombocyte aggregation inhibitors such as ticlopidine, clopidogrel, abciximab, dextrans; corticosteroids such as aidlometasones, estradiols, such as 17β-estradiol, amcinonides, augmented betamethasones, beclomethasones, betamethasones, budesonides, cortisones, clobetasol, clocortolones, desonides, desoximetasones, dexamethasones, flucinolones, fluocinonides, flurandrenolides, flunisolides, fluticasones, halcinonides, halobetasol, hydrocortisones, methylprednisolones, mometasones, prednicarbates, prednisones, prednisolones, triamcinolones; fibrinolytic agents such as tissue plasminogen activator, streptokinase, dipyridamole, ticlopidine, clopidine, and abciximab; non-steroidal anti-inflammatory drugs such as salicyclic acid and salicyclic acid derivatives, para-aminophenol derivatives, indole and indene acetic acids (e.g., etodolac, indomethacin, and sulindac), heteroaryl acetic acids (e.g., ketorolac, diclofenac, and tolmetin), arylpropionic acids (e.g., ibuprofen and derivatives thereof, anthranilic acids (e.g., meclofenamates and mefenamic acid), enolic acids (e.g., piroxicam, tenoxicam, phenylbutazone, and oxyphenthatrazone), gold compounds (e.g., auranofin, aurothioglucose, and gold sodium thiomalate), diflunisal, meloxicam, nabumetones, naproxen, oxaprozin, salsalate, celecoxib, rofecoxib; cytostatics such as alkaloids and podophyllum toxins such as vinblastin, vincristin; alkylants such as nitrosoureas and nitrogen lost analogues; cytotoxic antibiotics such as daunorubicin, doxorubicin, and other anthracyclins and related substances, bleomycin, and mitomycin; antimetabolites such as folic acid analogues, purine analogues and related inhibitors (e.g., mercaptopurine, thioguanine, pentostatin, and 2-chlorodeoxyadenosine), pyrimidine analogues (e.g., fluorouracil, floxuridine, and cytarabine), and platinum coordination complexes (e.g., cisplatinum, carboplatinum and oxaliplatinum); tacrolimus, azathioprine, cyclosporine, paclitaxel, docetaxel, sirolimus; amsacrin, irinotecan, imatinib, topotecan, interferon-alpha 2a, interferon-alpha 2b, hydroxycarbamide, miltefosin, pentostatin, porfimer, aldesleukin, bexarotene, and tretinoin; antiandrogens and antiestrogens; antiarrythmics, in particular antiarrhythmics of class I such as antiarrhythmics of the quinidine type (e.g., quinidine, dysopyramide, ajmaline, prajmalium bitartrate, and detajmium bitartrate); antiarrhythmics of the lidocaine type, (e.g., lidocaine, mexiletin, phenyloin, and tocainid); antiarrhythmics of class I C (e.g., propafenone, flecainide (acetate)); antiarrhythmics of class II, including betareceptor blockers such as metoprolol, esmolol, propranolol, metoprolol, atenolol, and oxprenolol; antiarrhythmics of class III such as amiodarone and sotalol; antiarrhythmics of class IV such as diltiazem, and verapamil; and other antiarrhythmics such as adenosine, orciprenaline, TC-912, and ipratropium bromide.

Other types of therapeutic agents may include digitalis glycosides such as acetyl digoxin/methyldigoxin, digitoxin, and digoxin; heart glycosides such as ouabain and proscillaridin; antihypertensives such as centrally effective antiadrenergic substances (e.g., methyidopa and imidazoline receptor agonists); calcium channel blockers of the dihydropyridine type, such as nifedipine and nitrendipine; ACE inhibitors (e.g., quinaprilate, cilazapril, moexipril, trandolapril, spirapril, imidapril, and trandolapril); angiotensin-II-antagonists (e.g., candesartancilexetil, valsartan, telmisartan, olmesartan medoxomil, and eprosartan); peripherally effective alpha-receptor blockers such as prazosin, urapidil, doxazosin, bunazosin, terazosin, and indoramin; vasodilators such as dihydralazine, diisopropyl amine dichloroacetate, minoxidil, and nitropiusside-sodium; other antihypertonics such as indapamide, codergocrin mesilate, dihydroergotoxin methane sulphonate, cicletanin, bosentan, and fluocortisone; phosphodiesterase inhibitors, such as milrinone and enoximone, as well as antihypotonics (e.g., adrenergics and dopaminergic substances such as dobutamine, epinephrine, etilefrine, norfenefrine, norepinephrine, oxilofrine, dopamine, midodrine, pholedrine, and amezinium methyl) and partial adrenoreceptor agonists (e.g., dihydroergotamine); fibronectin, polylysines and ethylene vinyl acetates; and adhesive substances such as cyanoacrylates, beryllium, and silica.

Additional therapeutic agents may also include antibiotics and anti-infectives such as β-lactam antibiotics (e.g., β-lactamase-sensitive penicillins, including benzyl penicillins (penicillin G) and phenoxymethylpenicillin (penicillin V)); β-lactamase-resistant penicillins, such as aminopenicillins, which include amoxicillin, ampicillin, and bacampicillin;

acylaminopenicillins such as mezlocillin and piperacillin; carboxypenicillines and cephalosporins (e.g., cefazolin, cefuroxim, cefoxitin, cefotiam, cefaclor, cefadroxil, cefalexin, loracarbef, cefixim, cefuroximaxetil, ceftibuten, cefpodoximproxetil, and cefpodoximproxetil); aztreonam, ertapenem, and meropenem; β-lactamase inhibitors such as sulbactam and sultamicillintosilates; tetracyclines such as doxycycline, minocycline, tetracycline, chlorotetracycline, oxytetracycline; aminoglycosides such as gentamicin, neomycin, streptomycin, tobramycin, amikasin, netilmicin, paromomycin, framycetin, and spectinomycin; makrolide antibiotics such as azithromycin, clarithromycin, erythromycin, roxithromycin, spiramycin, and josamycin; lincosamides such as clindamycin and lincomycin; gyrase inhibitors, such as fluoroquinolones, which include ciprofloxacin, ofloxacin, moxifloxacin, norfloxacin, gatifloxacin, enoxacin, fleroxacin, and levofloxacin; quinolones such as pipemidic acid; sulphonamides such as trimethoprim, sulphadiazin, and sulphalene; glycopeptide antibiotics such as vancomycin and teicoplanin; polypeptide antibiotics, such as polymyxins, which include colistin, polymyxin-b, and nitroimidazol derivatives (e.g., metronidazol and tinidazol); aminoquinolones such as chloroquin, mefloquin, and hydroxychloroquin; biguanides such as proguanil; quinine alkaloids and diaminopyrimidines such as pyrimethamine; amphenicols such as chloramphenicol; rifabutin, dapsone, fusidinic acid, fosfomycin, nifuratel, telithromycin, fusafungin, fosfomycin, pentamidindiisethionate, rifampicin, taurolidine, atovaquone, and linezolid; virostatics such as aciclovir, ganciclovir, famciclovir, foscamet, inosine (dimepranol-4-acetamidobenzoate), valganciclovir, valaciclovir, cidofovir, and brivudin; tyrosine kinase inhibitors; anti-apoptotic agents such as caspase inhibitors (e.g., fluoromethylketone peptide derivatives), calpain inhibitors, cathepsin inhibitors, nitric oxide synthase inhibitors, flavonoids, vitamin A, vitamin C, vitamin E, vitamin D, pycnogenol, super oxidedismutase, N-acetyl cysteine, selenium, catechins, alpha lipoic acid, melatonin, glutathione, zinc chelators, calcium chelators, and L-arginine; Coumadin; beta-blockers; diuretics; spirolactone; TC-313; and natural products such as vinca alkaloids (e.g., vinblastine, vincristine and vinorelbine).

As noted above, the therapeutic agent may also include a biological agent. The biological agent may include organic substances such as peptides, proteins, enzymes, carbohydrates (e.g., monosaccharides, oligosaccharides and polysacchardies), lipids, phospholipids, steroids, lipoproteins, glycoproteins, glycolipids, proteoglycans, polynucleotides (e.g., DNA and RNA), antisense polynucleotides (e.g., c-myc antisense), antibodies (e.g., monoclonal or polycolonal) and/or antibody fragments (e.g., anti-CD34 antibody), bioabsorbable polymers (e.g., polylactonic acid), chitosan, extracellular matrix modulators, such as matrix metalloproteinases (MMP), which include MMP-2, MMP-9 and Batimastat; and protease inhibitors.

Biological agents may include, for example, agents capable of stimulating angiogenesis in the myocardium. Such agents may include vascular endothelial growth factor (VEGF), basic fibroblast growth factor (bFGF), non-viral DNA, viral DNA, and endothelial growth factors (e.g., FGF-1, FGF-2, VEGF, TGF). Other growth factors may include erythropoietin and/or various hormones such as corticotropins, gonadotropins, thyrotrophin, desmopressin, terlipressin, oxytocin, cetrorelix, corticorelin, leuprorelin, triptorelin, gonadorelin, ganirelix, buserelin, nafarelin, and goserelin. Additional growth factors may also include cytokines, epidermal growth factors (EGF), platelet derived growth factor (PDGF), transforming growth factors-β (TGF-β), transforming growth factor-α (TGF-α), insulin-like growth factor-I (IGF-I), insulin-like growth factor-II (IGF-II), interleukin-1 (IL-1), interleukin-2 (IL-2), interleukin-6 (IL-6), interleukin-8 (IL-8), tumour necrosis factor-α (TNF-α), tumour necrosis factor-β (TNF-β), interferon-γ (INF-γ), colony stimulating factors (CSFs); monocyte chemotactic protein, and fibroblast stimulating factor 1.

Still other biological agents may include regulatory peptides such as somatostatin and octreotide; bisphosphonates (e.g., risedronates, pamidronates, ibandronates, zoledronic acid, clodronic acid, etidronic acid, alendronic acid, and tiludronic acid); fluorides such as disodium fluorophosphate and sodium fluoride; calcitonin and dihydrotachystyrene; histamine; fibrin or fibrinogen; endothelin-1; angiotensin II; collagens; bromocriptin; methylsergide; methotrexate; carbontetrachloride and thioacetamide.

The present invention may also be treated (i.e., seeded) with other biological agents, such as cells. Suitable cells may include any one or combination of eukaryotic cells. Additionally or optionally, the cells may be capable of producing therapeutic agents and/or genetically engineered to produce therapeutic agents. Suitable cells for use in the present invention include, for example, progenitor cells such as stem cells. The cells may be autologous or allogenic, genetically engineered or non-engineered, and may include, for example, mesenchymal or mesodermal cells, including, but not limited to, endothelial progenitor cells, endothelial cells, and fibroblasts. Mixtures of such cells can also be used.

A variety of ex vivo or in vivo methods can be used to deliver a nucleic acid molecule or molecules, such as a gene or genes, to the cells. For example, the cells can be modified (i.e., genetically engineered) to produce or secrete any one or combination of the above therapeutic agents, including, but not limited to, anticoagulant agents, antiplatelet agents, antifibrinolytic agents, angiogenesis factors, and the like. Ex vivo gene transfer is a process by which cells are removed from the body using well known techniques, genetically manipulated, usually through transduction or transfection of a nucleic acid molecule into the cells in vitro, and then returned to the body for therapeutic purposes. This contrasts with in vivo genetic engineering where a gene transfer vector or a liposome that contains specific genes is administered to a patient resulting in genetic transfer into cells and tissues in the intact patient. Ex vivo and in vivo gene transfer techniques are well known to one of skill in the art.

To treat the present invention with at least one therapeutic agent, a variety of methods, agents, and compositions may be used. For example, the therapeutic agent can be simply linked to the surface of the expandable support member 12, embedded and released from within polymer materials, such as a polymer matrix, or surrounded by and released through a carrier. Several approaches to treating medical devices with therapeutic agents exist. Some therapeutic agents can be loaded directly onto metallic surfaces; however, a coating composition, typically comprised of at least one polymer and at least one therapeutic agent, is usually used to treat drug-eluting devices. The coating composition ensures retention of the therapeutic agent during deployment and modulates elution kinetics of the therapeutic agent. By altering the release kinetics of different therapeutic agents in the same coating composition, distinct phases of a given disease process may be targeted.

The present invention may be treated with a coating composition comprising at least one therapeutic agent and at least one dendrimer, polymer or oligomer material. The dendrimer(s), polymer(s) and/or oligomer(s) may be of various types and from various sources, including natural or synthetic polymers, which are biocompatible, bioabsorbable and useful for controlled release of the therapeutic agent. For example, synthetic polymers can include polyesters, such as polylactic acid, polyglycolic acid, and/or combinations thereof, polyanhydrides, polycaprolactones, polyhydroxybutyrate valerates, and other bioabsorbable polymers or mixtures of copolymers thereof. Natural polymeric materials can include proteins such as collagen, fibrin, elastin, extracellular matrix components, other biologic agents, and/or mixtures thereof.

The polymer material or mixture thereof of the coating composition can be applied with the therapeutic agent on the surface of the present invention and can comprise a single layer. Optionally, multiple layers of the polymer material can be applied to form the coating composition. Multiple layers of the polymer material can also be applied between layers of the therapeutic agent. For example, the polymeric layers may be applied sequentially, with the first layer directly in contact with the uncoated surface of the apparatus and a second layer comprising the therapeutic agent and having one surface in contact with the first layer and the opposite surface in contact with a third layer of polymeric material which is in contact with the surrounding tissue. Additional layers of the polymeric material and therapeutic agent can be added as required.

Alternatively, the coating composition can be applied as multiple layers comprising one or more therapeutic agents surrounded by polymer material. For instance, the coating composition can comprise multiple layers of a single therapeutic agent, one or more therapeutic agents in each layer, and/or differing therapeutic agents in alternating layers. Alternatively, the layers comprising the therapeutic agent can be separated from one another by a layer of polymer material.

The coating composition may further comprise at least one pharmaceutically acceptable polymers and/or pharmaceutically acceptable carriers, for example, non-absorbable polymers, such as ethylene vinyl acetate and methylmethacrylate. The non-absorbable polymer, for example, can aid in further controlling release of the therapeutic agent by increasing the molecular weight of the coating composition and thereby delaying or slowing the rate of release of the therapeutic agent.

The coating composition can be applied to the present invention using standard techniques to cover the entire surface of the apparatus, or partially, as a single layer in a dot matrix pattern, for example. The coating composition can be applied using various techniques available in the art, such as dipping, spraying, vapor deposition, an injection-like and/or a dot matrix-like approach. Upon contact of the coating composition with adjacent tissue where implanted, the coating composition can begin to degrade in a controlled manner. As the coating composition degrades, the therapeutic agent is slowly released into adjacent tissue and the therapeutic agent is eluted so that the therapeutic agent can have its effect locally.

Where the therapeutic agent comprises a biological agent, such as cells, the biological agent can be coated directly onto the surface of the present invention or, alternatively, they can be incorporated into the polymeric material (e.g., into a polymer matrix). Such biological agents may also be included within at least one microscopic containment vehicle (e.g., a liposome, nanocapsule, nanoparticle, micelle, synthetic phospholipid, gas-dispersion, emulsion, microemulsion, nanosphere, and the like) that can be stimulated to release the biological agent(s) and/or that release the biological agent(s) in a controlled manner. The microscopic containment vehicle can be coated onto the surface of the present invention or incorporated into the polymeric material. Where the biological agent comprises cells, for example, the cells can be induced to produce, activate, and/or release their cellular products (including one or more therapeutic agents) by an external stimulation device (e.g., an electrical impulse). Alternatively, cells can constitutively release one or more therapeutic agents at a desired level.

Figure 6:
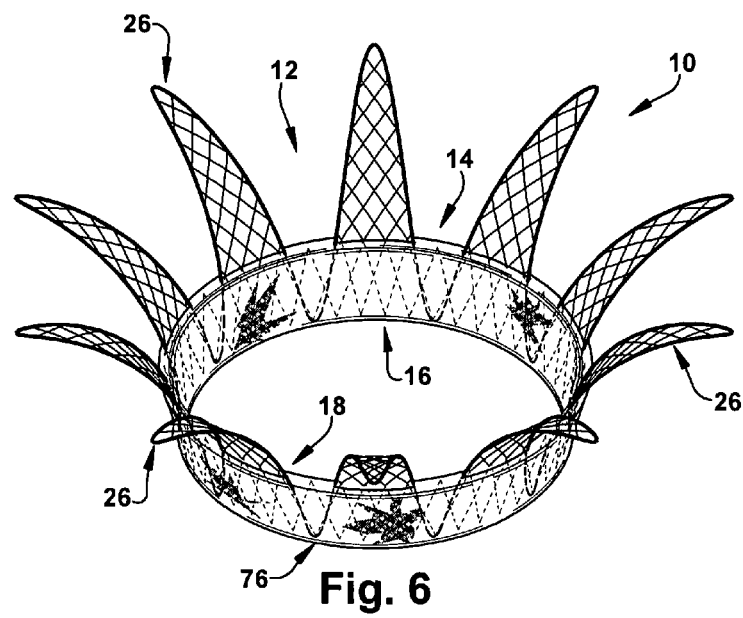
FIG. 6 is a perspective view showing another alternative embodiment of the apparatus in FIG. 1.

The present invention may further include a layer 76 of biocompatible material covering at least a portion of the expandable support member 12. As shown in FIG. 6, for example, the main body portion 18 may be covered with the layer 76 of biocompatible material. It will be appreciated, however, that the layer 76 of biocompatible material may cover any combination of other portions of the expandable support member 12, such as only the wing members 26 or both the wing members and the main body portion 18.

The layer 76 of biocompatible material may be a synthetic material such as Dacron® (Invista, Witchita, Kans.), Gore-Tex® (W. L. Gore & Associates, Flagstaff, Ariz.), woven velour, polyurethane, polytetrafluoroethylene (PTFE), expanded PTFE (ePTFE), or heparin-coated fabric. Alternatively, the layer 76 may be a biological material such as bovine or equine pericardium, peritoneal tissue, an allograft, a homograft, patient graft, or a cell-seeded tissue. The layer 76 can cover either the inside surface of the expandable support member 12, the outside surface of the expandable support member, or can be wrapped around both the inside and outside surfaces. The layer 76 may be attached around the entire circumference of the expandable support member 12 or, alternatively, may be attached in pieces or interrupted sections to allow the expandable support member to more easily expand and contract.

The expandable support member 12 may further comprise an electrical mechanism (not shown) for delivering electrical energy to a portion of the ostium 66 (FIG. 2) of a blood vessel 68. The electrical mechanism may comprise, for example, an antenna and a power source coupled to the expandable support member 12 (FIG. 1), along with an externally located device capable of generating an electrical energy signal. Delivery of electrical energy may be desirable where a conduction block or ablative procedure is needed, for example, and may be achieved by delivering radio frequency energy, microwave energy, laser, ultrasonic energy, freezing (i.e., cryoablation), or any other type of appropriate energy. To select for different capacitive and resistive effects, the expandable support member 12 may be formed from different biocompatible metals such as platinum iridum alloys, ND35N, titanium, Nitinol, and stainless steels. Depending on the construction of the electrical mechanism, the expandable support member 12 may operate by acting as an electrically insulative barrier to an electric signal, a capacitively coupled short across a region of tissue in question, an averager that reduces the effective signal of the region of tissue in question, or any combination of these mechanisms.

As shown in FIGS. 8-12, the present invention may be placed in a patient's pulmonary vein 46 to treat a cardiac disease such as AF, for example.

Using a percutaneous approach, the patient's left atrium 34 is first accessed. Once the left atrium 34 has been accessed, the dimensions of the pulmonary vein 46, the ostium 70 of the pulmonary vein, and the antrum 72 (FIG. 10) surrounding the ostium are determined. Various devices and methods for determining the dimensions of cardiac and vascular structures are known in the art.

After determining the dimensions of the pulmonary vein 46, the ostium 70 of the pulmonary vein, and the antrum 72, an appropriately-sized apparatus 10 is selected. More particularly, the selected apparatus 10 will be appropriately dimensioned to the size and shape of the pulmonary vein 46, the ostium 70 of the pulmonary vein, and the antrum 72 surrounding the ostium.

Figure 8:
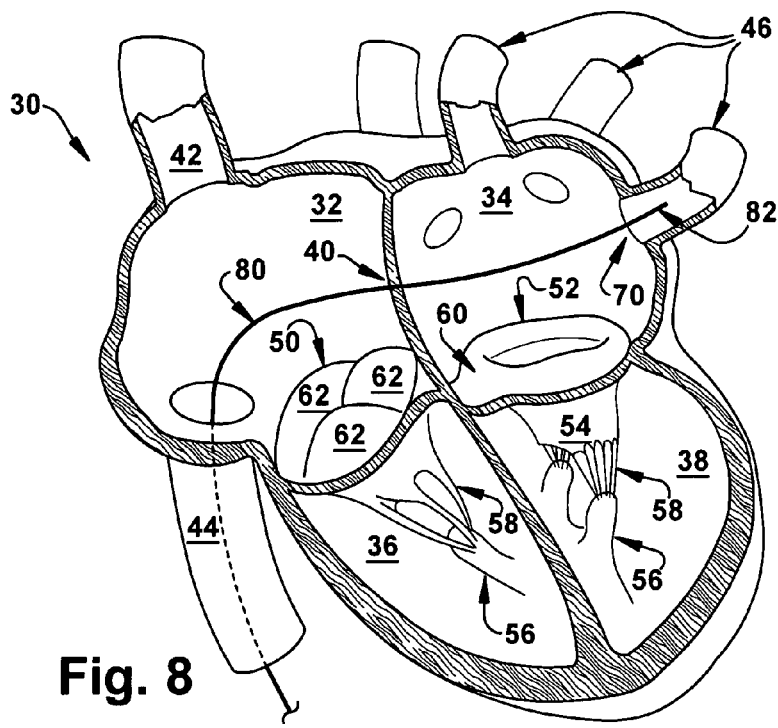
FIG. 8 is a cross-sectional view showing a guidewire extending trans-septally through the human heart.

Next, a guidewire 80 (FIG. 8) is inserted into a femoral vein (not shown) or jugular vein (not shown) and, under image guidance (e.g., fluoroscopy, ultrasound, magnetic resonance, computed tomography, or combinations thereof, respectively steered through the patient's vasculature into the inferior vena cava 44 or superior vena cava 42. The guidewire 80 is then passed across the right atrium 32 so that the distal end 82 of the guidewire pierces the interatrial septum 40 as shown in FIG. 8. The guidewire 80 is then extended across the left atrium 34 and into the pulmonary vein 46 so that the distal end 82 of the guidewire is securely positioned in the pulmonary vein.

Figure 9:
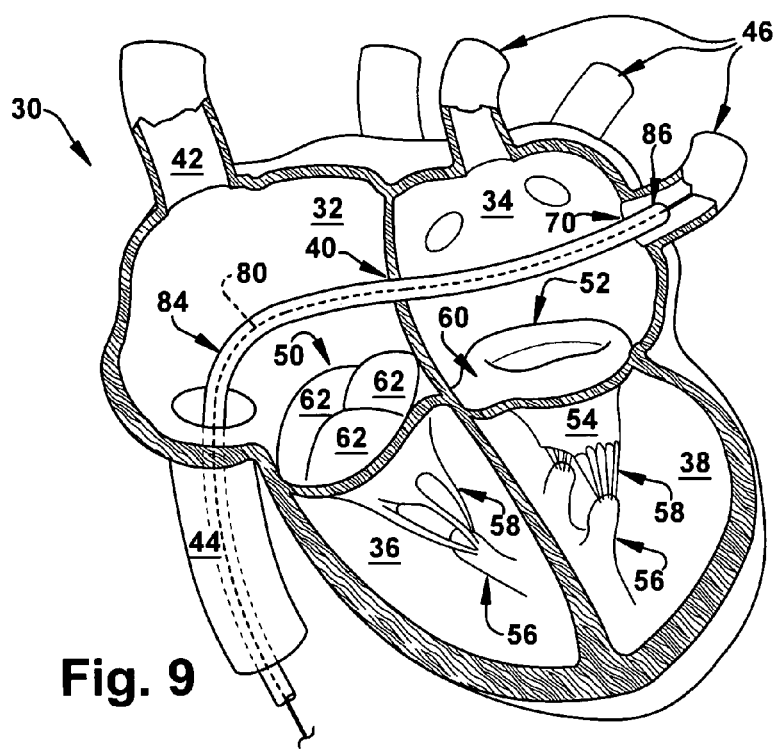
FIG. 9 is a cross-sectional view showing a catheter advanced over the guidewire.

After the guidewire 80 is passed into the pulmonary vein 46, a catheter 84 or sheath is passed over the guidewire as shown in FIG. 9. The catheter 84 may be comprised of a flexible, resiliently yieldable material such as silicone, PTFE, ePTFE, plastic polymer, or the like. The catheter 84 is urged along the guidewire 80 until the distal end 86 of the catheter is appropriately positioned in the ostium 70 of the pulmonary vein 46.

Figure 10:
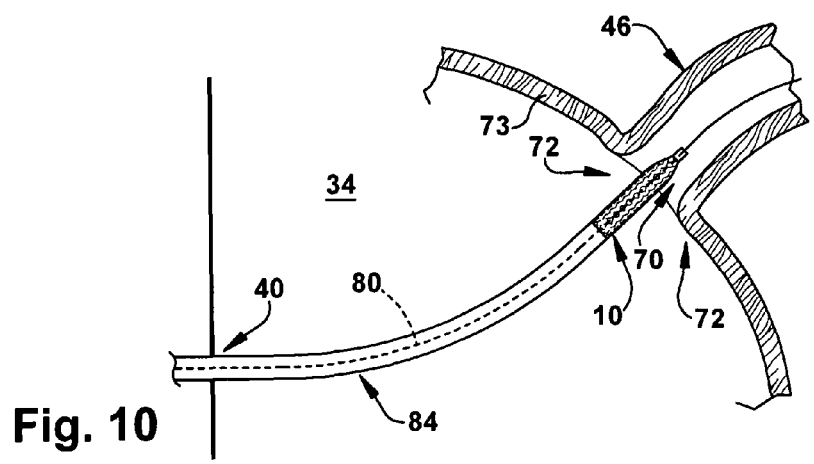
FIG. 10 is a cross-sectional view showing the apparatus in FIG. 1, in a collapsed configuration, contained in the catheter.
Figure 11:
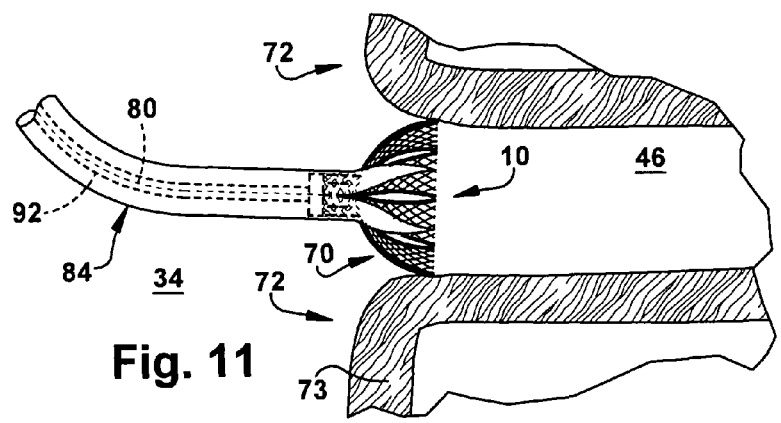
FIG. 11 is a cross-sectional view showing the apparatus of FIG. 1 at an initial stage of delivery in a pulmonary vein.

Next, the apparatus 10, in a collapsed configuration, is attached to a proximal end (not shown) of the guidewire 80, and a pushrod 92 (FIG. 11) or other similar device is then used to urge the apparatus along the guidewire into the left atrium 34 (FIG. 10). When the apparatus 10 is positioned near the distal end 86 of the catheter 84, the catheter is slowly withdrawn. As the catheter 84 is withdrawn, the main body portion 18 of the expandable support member 12 is progressively freed from the catheter and self-expands into the pulmonary vein 46 so that the main body portion engages the wall of the cardiac wall 73 (FIG. 11).

Figure 12:
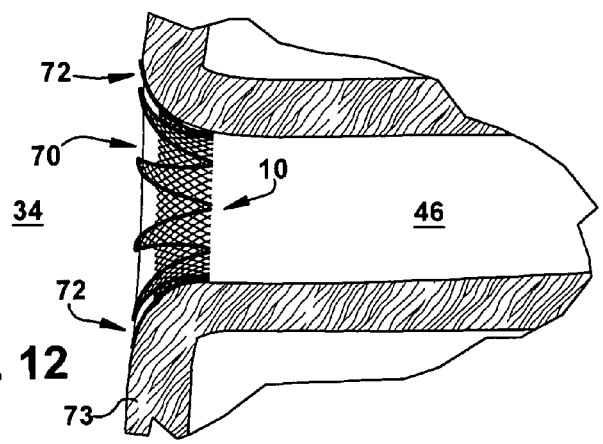
FIG. 12 is a cross-sectional view showing the apparatus of FIG. 1 being deployed in a pulmonary vein.

As the expandable support member 12 is further freed from the catheter 84, each of the wing members 26 expand to their radially expanded configuration. As shown in FIG. 12, each of the wing members 26 expands to engage the antrum 72 surrounding the ostium 70 of the pulmonary vein 46. Where the wing members 26 also comprise the attachment mechanism 28 shown in FIG. 7, the hook members 29 are embedded into the antrum 72 surrounding the ostium 70 of the pulmonary vein 46 and the cardiac wall 73 as the wing members expand into their radially expanded configuration. Once the expandable support member 12 has obtained its expanded configuration, the expandable support member is securely positioned in the ostium 70 of the pulmonary vein 46, and the catheter 84 and guidewire 80 may be withdrawn from the patient. The position of the apparatus 10 may then be varied as needed. For example, the main body portion 18 of the apparatus 10 may be moved either more proximate to, or less proximate from, the ostium 70.

Figure 13:
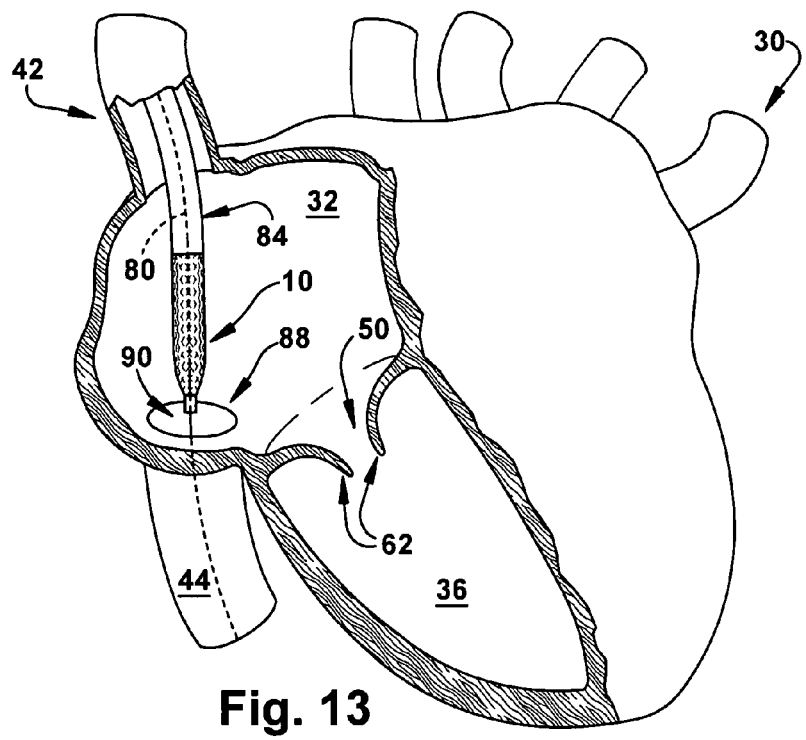
FIG. 13 is a cross-sectional view showing an alternative embodiment of the apparatus in FIG. 1, in a collapsed configuration, extending into the right atrium of the human heart.
Figure 14:
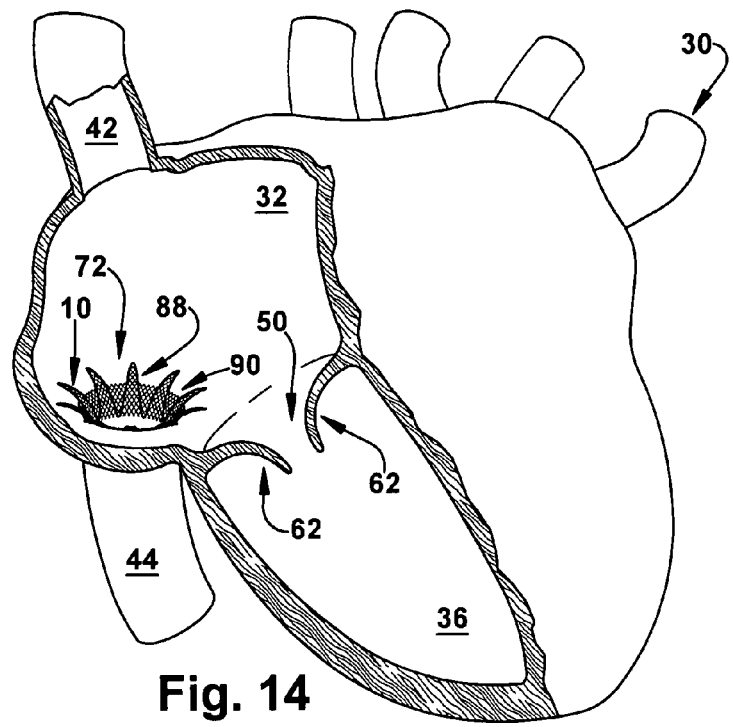
FIG. 14 is a cross-sectional view showing the apparatus in FIG. 13 deployed in the inferior vena cava of the human heart.

In an alternative embodiment of the present invention, the expandable support member 12 may be placed in either the inferior vena cava 44 or the superior vena cava 42. FIGS. 13 and 14 illustrate placement of the apparatus 10 in the inferior vena cava 44.

Using a percutaneous approach, the patient's right atrium 32 may first be accessed. Once the right atrium 32 has been accessed, the dimensions of the inferior vena cava 44, the ostium 90 of the inferior vena cava, and the antrum 72 (FIG. 14) surrounding the inferior vena cava can be determined. Various devices and methods for determining the dimensions of cardiac and vascular structures are known in the art.

After determining the dimensions of the inferior vena cava 44, the ostium 90 of the inferior vena cava, and the antrum 72 surrounding the ostium, an appropriately-sized apparatus 10 is selected. More particularly, the selected apparatus 10 will be appropriately dimensioned to the size and shape of the inferior vena cava 44, the ostium 90 of the inferior vena cava, and the antrum 72 surrounding the ostium.

Next, a guidewire 80 is inserted into the patient's jugular vein (not shown) and, under image guidance (e.g., fluoroscopy, ultrasound, magnetic resonance, computed tomography, or combinations thereof), steered through the superior vena cava 42 into the right atrium 32. Once the guidewire 80 is delivered to the right atrium 32 and secured in the inferior vena cava 44, a catheter 84 or sheath is passed over the guidewire and advanced into the right atrium as shown in FIG. 13. The distal end 86 of the catheter 84 may then be positioned at the ostium 90 of the inferior vena cava 44 and the apparatus 10, in a collapsed configuration, attached to a proximal end (not shown) of the guidewire 80 and then urged into the right atrium 32.

The catheter 84 may then be slowly withdrawn so that the apparatus 10 is progressively freed from the catheter and the main body portion 18 self-expands into the inferior vena cava 44. The catheter 84 may then be withdrawn further so that the wing members 26 are freed from the catheter and move from a collapsed configuration to a radially expanded configuration. As the wing members 26 obtain the radially expanded configuration, the wing members engage the antrum 72 surrounding the ostium 90 of the inferior vena cava 44 (FIG. 14). Consequently, the expandable support member 12 is securely positioned in the ostium 90 of the inferior vena cava 44, and the guidewire 80 and catheter 84 are withdrawn from the patient.

It will be appreciated by one having ordinary skill in the art that the apparatus 10 may implanted using non-percutaneous techniques. For example, an open-chest procedure may be used to implant the apparatus 10 as either a stand alone procedure or as a complement to valve and/or heart transplant surgery. Additionally, it will be appreciated that the apparatus 10 could be implanted either after or during a surgical procedure, such as a CABG procedure, for example.

From the above description of the invention, those skilled in the art will perceive improvements, changes and modifications. For example, it is contemplated that, in addition to the self-expanding apparatus 10 disclosed herein, a balloon (not shown) or mechanical-based apparatus (not shown) could be used to deliver and deploy the expandable support member 12 described herein. Additionally, it is contemplated that the apparatus 10 may be implanted in other cardiac structures, such as the ostium of a coronary artery (not shown) or some other vascular bifurcation. Such improvements, changes and modifications within the skill of the art are intended to be covered by the appended claims.

Having described the invention, we claim:

1. An apparatus for placement in a blood vessel to treat cardiac arrhythmias, said apparatus comprising:
    an expandable support member having a first mesh-like configuration, wherein at least a portion of the expandable support member is treated with a therapeutic agent;
    a plurality of wing members that extend from only a proximal end of said expandable support member, each of said plurality of wing members independently having a second mesh-like configuration, each of said plurality of wing members being radially spaced apart from one another, and each of said plurality of wing members having a free end shaped to conform to a portion of an antrum of a cardiac chamber surrounding the blood vessel to engage with the portion of the antrum of the cardiac chamber surrounding the blood vessel; and an electrical mechanism coupled to said expandable support member for delivering electrical energy to at least a portion of an ostium of the blood vessel to ablate tissue.

2. The apparatus of claim 1 wherein said expandable support member, in its expanded form, is shaped to conform to the shape of at least a portion of the blood vessel.

3. The apparatus of claim 1 wherein each of said wing members extends beyond the proximal end of the expandable support member:
wherein the proximal end of the expandable support member extends with a portion of each of the wing members.

4. The apparatus of claim 1 wherein a plurality of portions of said expandable support member are separately treated with a different one of a plurality of therapeutic agents.

5. The apparatus of claim 1, wherein each of said plurality of wing members is separately treated with a therapeutic agent.

6. The apparatus of claim 5, wherein each of said plurality of wing members is separately treated with a different one of a plurality of therapeutic agents.

7. The apparatus of claim 1 wherein a portion of said expandable support member is bioabsorbable.

8. The apparatus of claim 1 further comprising an inflatable balloon configured to expand said expandable support member to engage the at least the portion of the ostium of the blood vessel.

9. The apparatus of claim 1 further comprising a capsule containing said expandable support member in a collapsed configuration,
wherein said capsule is removable to allow said expandable support member to expand into the at least the portion of the ostium of the blood vessel.

10. The apparatus of claim 1, wherein at least a portion of said expandable support member is covered with a layer of biocompatible material selected from the group consisting of GORE-TEX and expanded PTFE.

11. The apparatus of claim 1, wherein each of said plurality of wing members has an arch-like shape.

12. The apparatus of claim 1, wherein said expandable support member is configured to elute the therapeutic agent into the blood vessel or the cardiac chamber.

13. The apparatus of claim 1, wherein the first mesh-like configuration is different from the second mesh-like configuration.

14. An apparatus for placement in a blood vessel to treat a cardiac arrhythmia, said apparatus comprising:
an expandable support member comprising a first wire-mesh configuration, wherein at least a portion of said expandable support member is treated with a therapeutic agent;
a plurality of arch-shaped wing members extending from a proximal end of said expandable support member and being radially spaced apart from one another, each of said plurality of wing members independently comprising a second wire-mesh configuration, and each of said plurality of wing members having a free end adapted for engaging a portion of an antrum of a cardiac chamber surrounding the blood vessel; and
an electrical mechanism coupled to said expandable support member for delivering electrical energy to at least a portion of an ostium of the blood vessel to ablate tissue.

15. The apparatus of claim 14, wherein at least one of the plurality of wing members is treated with a second therapeutic agent.

16. The apparatus of claim 15, wherein the therapeutic agent comprises an anti-inflammatory therapeutic agent and the second therapeutic agent comprises an anti-coagulant therapeutic agent.

17. The apparatus of claim 14, wherein each of said wing members extends beyond the proximal end of the expandable support member.

18. The apparatus of claim 17, wherein the proximal end of the expandable support member extends with a portion of each of the wing members.

19. The apparatus of claim 18, wherein the proximal end of the expandable support member extends with 50% or less of each of the wing members.

20. An apparatus configured to be placed in a blood vessel, said apparatus comprising:
an expandable support member comprising a first wire-mesh configuration, wherein at least a portion of said expandable support member is treated with a therapeutic agent;
a plurality of wing members extending from a proximal end of said expandable support member, each of said plurality of wing members independently comprising a second wire-mesh configuration different from the first wire-mesh configuration, and each of said plurality of wing members having a free end adapted for engaging a portion of an antrum of a cardiac chamber surrounding the blood vessel,
wherein each of the plurality of wing members comprises an arch-shaped perimeter that bounds the second wire-mesh configuration; and
an electrical mechanism coupled to said expandable support member for delivering electrical energy to at least a portion of an ostium of the blood vessel to ablate tissue.

21. The apparatus of claim 20, wherein the proximal end of the expandable support member extends up to less than the entire perimeter of each of the plurality of wing members.

* * * * *